US012661507B2

(12) United States Patent
Voloshin-Sela et al.

(10) Patent No.: US 12,661,507 B2
(45) Date of Patent: Jun. 23, 2026

(54) METHODS OF TREATING NEURODEGENERATIVE DISORDERS WITH ALTERNATING ELECTRIC FIELDS

(71) Applicant: Novocure GmbH, Root (CH)

(72) Inventors: Tali Voloshin-Sela, Haifa (IL); Lilach Avigdor, Haifa (IL); Eyal Dor-On, Haifa (IL); Moshe Giladi, Haifa (IL); Hila Fishman, Haifa (IL)

(73) Assignee: Novocure GmbH, Baar (CH)

( * ) Notice: Subject to any disclaimer, the term of this patent is extended or adjusted under 35 U.S.C. 154(b) by 382 days.

(21) Appl. No.: 17/716,431

(22) Filed: Apr. 8, 2022

(65) Prior Publication Data

US 2022/0323753 A1      Oct. 13, 2022

Related U.S. Application Data

(60) Provisional application No. 63/172,275, filed on Apr. 8, 2021.

(51) Int. Cl.
*A61N 1/36* (2006.01)
*A61N 1/32* (2006.01)

(52) U.S. Cl.
CPC ........... *A61N 1/36025* (2013.01); *A61N 1/32* (2013.01)

(58) Field of Classification Search
CPC .............................. A61N 1/36025; A61N 1/31
See application file for complete search history.

(56) References Cited

U.S. PATENT DOCUMENTS

| | | | |
|---|---|---|---|
| 5,233,987 | A | 8/1993 | Fabian et al. |
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |

(Continued)

FOREIGN PATENT DOCUMENTS

| | | |
|---|---|---|
| CN | 108289930 A | 7/2018 |
| CN | 111655319 A | 9/2020 |

(Continued)

OTHER PUBLICATIONS

Jiang XY, Chen TK, Zhou JT, He SY, Yang HY, Chen Y, Qu W, Feng F, Sun HP. Dual GSK-3B/AChE Inhibitors as a New Strategy for Multitargeting Anti-Alzheimer's Disease Drug Discovery. ACS Med Chem Lett. Feb. 9, 2018;9(3):171-176. (Year: 2018).*

(Continued)

*Primary Examiner* — Michael W Kahelin
*Assistant Examiner* — Attiya Sayyada Hussaini
(74) *Attorney, Agent, or Firm* — Potomac Law Group, PLLC

(57) ABSTRACT

Methods of treating a neurodegenerative disorder in a subject are provided by applying alternating electric fields to the brain of the subject, optionally also administering a drug for treatment of the neurodegenerative disorder (e.g., Alzheimer's disease, Parkinson's disease, dementia) to the subject. In some instances, the neurodegenerative disorder can be treated by applying alternating electric fields to a brain of the human subject wherein the brain is tumor-free.

8 Claims, 3 Drawing Sheets

(56) References Cited

U.S. PATENT DOCUMENTS

| | | | |
|---|---|---|---|
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,911,342 B2 * | 12/2014 | Dissing ................... A61P 25/00 |
| | | | 607/45 |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 11,191,956 B2 | 12/2021 | Giladi et al. |
| 2006/0167499 A1 | 7/2006 | Palti |
| 2007/0225766 A1 | 9/2007 | Palti |
| 2007/0239213 A1 | 10/2007 | Palti |
| 2008/0208287 A1 * | 8/2008 | Palermo ................. A61N 1/323 |
| | | | 607/3 |
| 2009/0076366 A1 | 3/2009 | Palti |
| 2012/0283726 A1 | 11/2012 | Palti |
| 2014/0296752 A1 | 10/2014 | Edgerton et al. |
| 2014/0330268 A1 | 11/2014 | Palti et al. |
| 2016/0016014 A1 * | 1/2016 | Wagner ................... A61N 1/32 |
| | | | 601/2 |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2019/0351231 A1 | 11/2019 | Meyre et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 * | 2/2020 | Hagemann ........ A61M 37/0092 |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0188672 A1 | 6/2020 | Charles et al. |
| 2020/0219261 A1 | 7/2020 | Shamir et al. |
| 2020/0269037 A1 | 8/2020 | Hagemann et al. |
| 2020/0269041 A1 | 8/2020 | Zeevi et al. |
| 2020/0368525 A1 | 11/2020 | Maag et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0187277 A1 | 6/2021 | Wasserman et al. |
| 2021/0196348 A1 | 7/2021 | Wasserman |
| 2021/0199640 A1 | 7/2021 | Patel et al. |
| 2021/0203250 A1 | 7/2021 | Wasserman |
| 2021/0268247 A1 | 9/2021 | Story et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |
| 2021/0379362 A1 | 12/2021 | Smith et al. |
| 2021/0408383 A1 | 12/2021 | Kalra et al. |
| 2022/0095997 A1 | 3/2022 | Wasserman |
| 2022/0096821 A1 | 3/2022 | Kirson et al. |
| 2022/0118249 A1 | 4/2022 | Bomzon et al. |
| 2022/0161028 A1 | 5/2022 | Giladi et al. |
| 2022/0193435 A1 | 6/2022 | Wasserman et al. |

FOREIGN PATENT DOCUMENTS

| | | | |
|---|---|---|---|
| JP | 2008506464 A | 3/2008 |
| WO | WO-2019012556 A1 * | 1/2019 | ......... A61N 1/36025 |
| WO | 2021137094 A1 | 7/2021 |

OTHER PUBLICATIONS

Cao, Lin, Jin Pu, and Min Zhao. "GSK-3↑² is essential for physiological electric field-directed Golgi polarization and optimal electrotaxis." Cellular and Molecular Life Sciences 68 (2011): 3081-3093. (Year: 2011).*

Beitz, "Parkinson's Disease: a review," Frontiers in Bioscience, S6, pp. 65-74, Jan. 2014.

Cai et al., "Roles of glycogen synthase kinase 3 in Alzheimer's disease," Current Alzheimer Research, vol. 9, No. 7, pp. 864-879, Jan. 2012.

Credle et al., "GSK-3β dysregulation contributes to parkinson's-like pathophysiology with associated region-specific phosphorylation and accumulation of tau and α-synuclein," Cell Death and Differentiation, vol. 22, pp. 838-851, May 2015.

Furlong et al., "The Parkinson's disease gene PINK1 activates Akt via PINK1 kinase-dependent regulation of the phospholipid PI(3,4,5)P3," Journal of Cell Science, vol. 132, Issue 20, Oct. 2019.

Hooper et al., "The GSK3 hypothesis of Alzheimer's disease," Journal of Neurochemistry, vol. 104, pp. 1433-1439, Dec. 2007.

International Search Report and Written Opinion issued in application No. PCT/IB2022/053329 dated Jun. 29, 2022.

Llorens-Martin et al., "GSK-3β, a pivotal kinase in Alzheimer disease, Frontiers in Molecular Neuroscience," vol. 21, No. 7, Article 46, May 2014.

Phiel et al., "GSK-3α regulates production of Alzheimer's disease amyloid-62 peptides," Naure, vol. 423, pp. 435-439, May 2003).

Sen et al., "Sulfhydration of AKT triggers Tau-phosphorylation by activating glycogen synthase kinase 3β in Alzheimer's disease," Neuroscience, vol. 117, No. 8, pp. 4418-4427, Feb. 2020.

Soutar et al., "Evidence that glycogen synthase kinase-3 isoforms have distinct substrate preference in the brain," Journal of Neurochemistry, vol. 115, pp. 974-983, Sep. 2010.

Uemura et al., "GSK3beta activity modifies the localization and function of presenilin 1," The Journal of Biological Chemistry, vol. 282, No. 21, pp. 15823-15832, May 2007.

Walsh et al., "Alzheimer's Disease and the Amyloid β-Protein," Progress in Molecular Biology and Translational Science, vol. 107, pp. 101-124, 2012.

(56)                    References Cited

OTHER PUBLICATIONS

Voloshin et al., "Tumor Treating Fields (TTFields) Hinder Cancer
Cell Motility through Regulation of Microtubule and Actin Dynam-
ics," Cancers, vol. 12, 3016; doi:10.3390/cancers12103016, Oct.
2020.

* cited by examiner

METHODS OF TREATING NEURODEGENERATIVE DISORDERS WITH ALTERNATING ELECTRIC FIELDS

CROSS REFERENCE TO RELATED APPLICATIONS

This application claims the benefit of U.S. Provisional Application 63/172,275, filed Apr. 8, 2021, which is incorporated herein by reference in its entirety.

BACKGROUND

Alternating electric fields (also known as Tumor Treating Fields (TTFields)) are used to disrupt cell division by applying low intensity, intermediate frequency (e.g., 50-500 kHz), alternating electric fields to cells in a target region of a body.

In the in vivo context, alternating electric field therapy can be delivered using a wearable and portable device (Optune®). The delivery system includes an electric field generator, four adhesive patches (non-invasive, insulated transducer arrays), rechargeable batteries and a carrying case. The transducer arrays are applied to the skin and are connected to the device and battery. The therapy is designed to be worn for as many hours as possible throughout the day and night. In the preclinical setting, TTFields can be applied in vitro using, for example, the Inovitro™ TTFields lab bench system. Inovitro™ includes a TTFields generator and base plate containing 8 ceramic dishes per plate. Cells are plated on cover slips placed inside each dish. TTFields are applied using two perpendicular pairs of transducer arrays insulated by a high dielectric constant ceramic in each dish. In both the in vivo and in vitro contexts, the orientation of the TTFields is switched 90° every 1 second, thus covering different orientation axes of cell divisions.

Neurodegenerative disorders (e.g., Alzheimer's disease, Parkinson's disease, and dementia) affect millions of people each year. These conditions generally relate to progressive damage to cells (e.g., brain cells) and nervous system connections.

Alzheimer's disease (AD) is associated with dementia and memory loss and affects 25 million people worldwide. There are currently no effective preventative or curative treatments. Amyloid β-protein (Aβ) is associated with causation of AD and is associated with formation of plaques in the brains of patients. Aβ proteins can form oligomeric assemblies that are associated with that memory impairment and subsequent neurodegeneration. Walsh et. al., *Alzheimer's disease and the amyloid β-protein*, Prog Mol Biol Transl Sci., 2012; 107:101-24.

Parkinson's disease (PD) is associated with loss of control over movement and is the second most common progressive neurodegenerative disorder. PD results from pathophysiologic loss or degeneration of dopaminergic neurons in the substantia nigra of the midbrain and the development of neuronal Lewy Bodies. Beitz, *Parkinson's disease: a review*, Front Biosci (Schol Ed) 2014 Jan. 1; 6:65-74. Effective therapies for PD are not yet available.

SUMMARY

Glycogen synthase kinase 3 beta (GSK3β) is a proline-directed serine-threonine kinase known to phosphorylate and inactivate glycogen synthase. GSK3β has been implicated in the production and accumulation of Aβ in Alzheimer's disease. Cai et al., *Roles of glycogen synthase kinase 3*

*in Alzheimer's disease*, Curr Alzheimer Res. 2012 September; 9(7):864-79; Hooper et al., *The GSK3 hypothesis of Alzheimer's disease*, J Neurochem. 2008 March; 104(6): 1433-1439; Sen et. al., *Sulfhydration of AKT triggers Tau-phosphorylation by activating glycogen synthase kinase 3β in Alzheimer's disease*, PNAS Feb. 25, 2020 117 (8) 4418-4427. GSK3β has been shown to be activated in neurodegenerative diseases such as Alzheimer's disease. In addition, inhibition of GSK3β reduces Aβ pathology.

GSK3β is regulated via Akt pathway which is also impaired in Parkinson's disease. Furlong et. al., *The Parkinson's disease gene PINK1 activates Akt via PINK1 kinase-dependent regulation of the phospholipid PI(3,4,5)P$_3$*, Journal of Cell Science (2019) 132; Credle et al., *GSK-3β dysregulation contributes to parkinson's-like pathophysiology with associated region-specific phosphorylation and accumulation of tau and α-synuclein*, Cell Death Differ. 2015 April; 22(5): 838-851.

Taken together, it is believed that inhibition of GSK3β via phosphorylation can be used to treat, reduce symptoms of, or inhibit development of neurodegenerative disorders such as AD and PD.

In one aspect, a first method is provided comprising treating a neurodegenerative disorder in a subject by administering a GSK3β inhibitor to the subject and applying alternating electric fields to a brain of the subject. In an aspect, the neurodegenerative disorder may be Alzheimer's disease (AD), amyotrophic lateral sclerosis (ALS), dementia, or Parkinson's disease.

In another aspect, a method is provided comprising treating a neurodegenerative disorder in a subject by administering a therapeutic drug and applying alternating electric fields to a brain of the subject. In an aspect, the therapeutic drug may be an anti-amyloid monoclonal antibody to the subject and applying alternating electric fields to a brain of the subject. In another aspect, the therapeutic drug may be a GSK3β inhibitor, a cholinesterase inhibitor, or an anti-amyloid monoclonal antibody. In another aspect, the GSK3β inhibitor is a cholinesterase inhibitor. In another aspect, the therapeutic drug may be a dopamine agonist, a monoamine oxidase B (MAO-B) inhibitor, a catechol O-methyltransferase inhibitor, or an anticholinergic.

In another aspect, a second method is provided comprising treating a neurodegenerative disorder in a subject by administering an anti-amyloid monoclonal antibody to the subject and applying alternating electric fields to a brain of the subject. In an aspect, the anti-amyloid monoclonal antibody may be aducanumab.

In a further aspect, a third method is provided comprising treating Parkinson's disease in a subject by administering 1-3,4-dihydroxyphenylalanine to the subject and applying alternating electric fields to a brain of the subject.

In another aspect, the above methods include administering one or more of the therapeutic drugs 9-ING-41, HY-130795, TWS119, Tideglusib, SAR502250, AR-A014418, TDZD8, Kenpaullone, Cromoyb sodium, SB415286, IM-12, CP21R7, GNF4877, 1-Azakenpaullone, or Indirubin-3'-monoxime, tacrine, galantamine, liquiritigenin, memantine, rivastigmine, donepezil, ciprofloxacin, celecoxib, tauroursodeoxycholic acid, sodium phenylbutyrate, levodopa, carbidopa, pramipexole, ropinirole, rotigotine, apomorphine, selegiline, rasagiline, safinamide, entacapone, opicapone, tolcapone, benztropine, trihexyphenidyl, amantadine, riluzole, or edaravone, 1-3,4-dihydroxyphenylalanine, or aducanumab. In an aspect the therapeutic drugs may be administered in combinations such as ciprofloxacin and celecoxib, or tauroursodeoxycholic acid and sodium phenylbutyrate.

Further aspects provide methods of treating a neurodegenerative disorder in a human subject by applying alternating electric fields to a brain of the human subject wherein the brain is tumor-free, wherein the subject is not diagnosed as having a tumor prior to applying the alternating electric fields, or further comprising diagnosing the subject with a neurodegenerative disorder.

DETAILED DESCRIPTION

Figure 1:
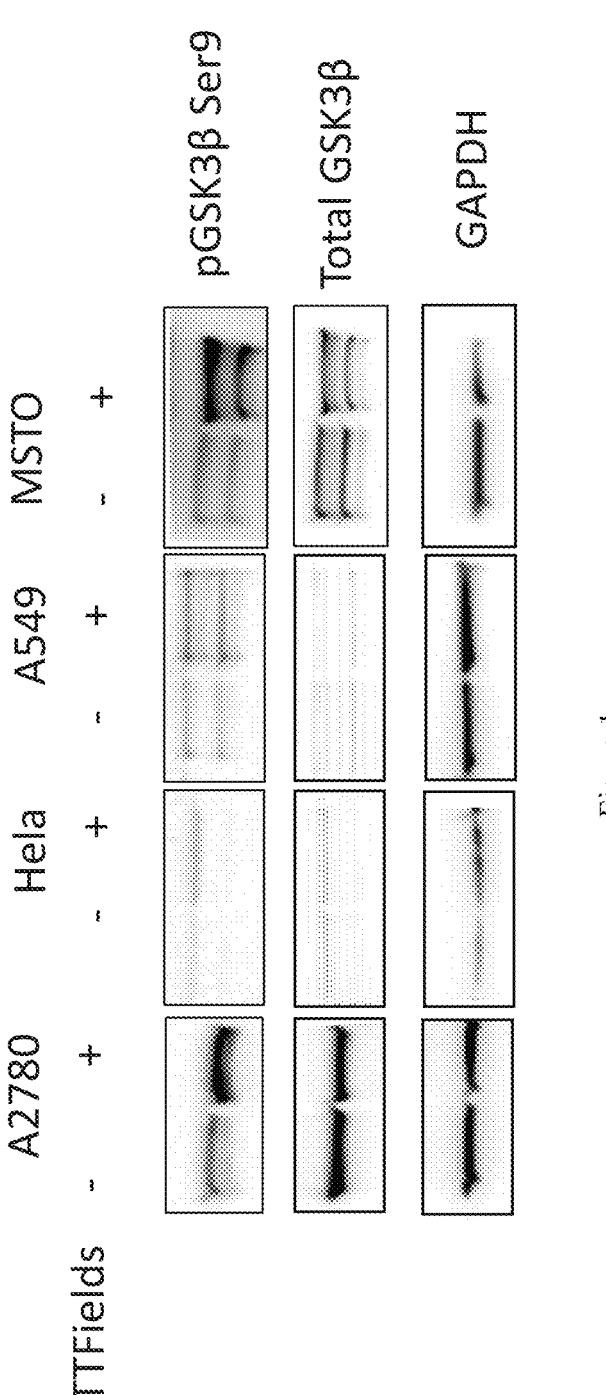
FIG. 1 provides an exemplary Western blot analysis of total GSK3β, GSK3β phosphorylated on Ser9 (pGSK3β Ser9), and GAPDH (Glyceraldehyde 3-phosphate dehydrogenase; a housekeeping protein) in control cell lysates compared with cells that were treated with alternating electric fields (TTFields) for 72 hours.

All references cited herein, including but not limited to patents and patent applications, are incorporated herein by reference in their entirety.

As described herein, alternating electric fields can be applied to the brain or regions of a brain of a subject's body to inhibit the activity of GSK3β through phosphorylation, for example, on serine 9, prior to or during treatment for a neurodegenerative condition such as AD, PD, or dementia. Without being bound by theory, it is believed that the combination of treating the brain with alternating electric fields in combination with standard of care treatment for neurodegenerative diseases can synergistically enhance treatment for or prevention of the neurodegenerative disease.

As described herein, TTFields reduce activity of GSK3β. GSK3β activation has been shown to be upregulated in neurodegenerative diseases such as Alzheimer's disease. Inhibition of GSK3β has been shown to improve the neurological state in mice. Llorens-Martin et al. *GSK-3β, a pivotal kinase in Alzheimer's disease*, Front Mol Neurosci. 2014; 7:46. GSK3β has also been implicated in Parkinson's disease. Credle et al., *GSK-3β dysregulation contributes to parkinson's-like pathophysiology with associated region-specific phosphorylation and accumulation of tau and α-synuclein*, Cell Death Differ. 2015 April; 22(5): 838-851.

For example, as described herein, GSK3β has been implicated in the production and accumulation of Aβ protein in Alzheimer's disease. In addition, GSK3β is regulated via Akt pathway which is also impaired in Parkinson's disease.

In AD patients, the abundance of phosphorylated Akt with active GSK3β implies that phosphorylated Akt was unable to inactivate GSK3β. Sen et. al., *Sulfhydration of AKT triggers Tau-phosphorylation by activating glycogen synthase kinase 3β in Alzheimer's disease*, PNAS Feb. 25, 2020 117 (8) 4418-4427. Total Akt and phosphorylated Akt was sulfhydrated at C77 due to the induction of intracellular hydrogen sulfide ($H_2S$). The increase in intracellular $H_2S$ levels resulted from the induction of the proinflammatory cytokine, IL-1β, a pathological hallmark of AD. Sulfhydrated Akt does not interact with GSK3β, and therefore does not phosphorylate GSK3β.

Tau overexpression disrupts axonal transport, causing vesicular aggregation, a phenomenon reversed by GSK-3β inhibitors. Soutar et al., *Evidence that glycogen synthase kinase-3 isoforms have distinct substrate preference in the brain*, J Neurochem. 2010 November; 115(4):974-83. Consistent with this, GSK-3β inhibition has been shown to reduce Aβ production in AD murine models. Phiel et al., *GSK-3alpha regulates production of Alzheimer's disease amyloid-beta peptides*, Nature. 2003 May 22; 423(6938): 435-9.

In vitro studies suggest that GSK-3β affects PS1 function, which is required for the generation of the toxic Aβ. Uemura et al., *GSK3beta activity modifies the localization and function of presenilin 1*, J Biol Chem. 2007 May 25; 282(21): 15823-32.

Applying alternating electric fields to the brain or regions of the brain can be used to inhibit activation of GSK3β in combination with treatment of a subject with GSK3β inhibitors and other drugs for treatment of neurodegenerative disorders.

The alternating electric fields discussed herein are similar to tumor treating fields (TTFields) and may be applied using hardware that is similar to Novocure's Optune® device, either at the same 200 kHz frequency that Optune uses, or at a different frequency (e.g., 50 kHz to 1 MHz). The size and shape of the transducer arrays that are used to apply the alternating electric fields to the subject's body will vary depending on the anatomical location to which the alternating electric fields are applied. The term "TTFields" as used herein and in the Figures is synonymous with the term "alternating electric fields."

In one aspect, a first method is provided comprising treating a neurodegenerative disorder in a subject by applying alternating electric fields to the brain of the subject.

In some instances, the neurodegenerative disorder is Alzheimer's disease, Parkinson's disease, dementia, or amyotrophic lateral sclerosis (ALS).

In some instances, at least a portion of the applying step is performed simultaneously with at least a portion of the administering step. In some instances, the applying step has a duration of at least 24 hours, 48 hours, 72 hours, 7 days, 14 days, 30 days or longer. The applying step can be continuous or discontinuous with breaks (e.g., breaks at 1, 2, 3, 6, 12, or 24 hours).

In some instances, the frequency of the alternating electric fields is between 50 and 1 MHz, between 75 and 500 kHz, between 80 kHz and 300 kHz, between 100 kHz and 200 kHz, or 150 kHz.

In an aspect, a second method is provided comprising treating a neurodegenerative disorder in a subject by applying alternating electric fields to the brain of the subject and further administering a therapeutic drug. For example, the therapeutic drug may include one or more of a GSK3β inhibitor, a cholinesterase inhibitor and an anti-amyloid monoclonal antibody. In some instances, the GSK3β inhibitor is a cholinesterase inhibitor.

For example, the therapeutic drug may be one or more of tacrine, galantamine, liquiritigenin, memantine, rivastigmine, and donepezil. In some instances, the GSK3β inhibitor or cholinesterase inhibitor is one or more of tacrine, galantamine, liquiritigenin, memantine, rivastigmine, and donepezil.

In some instances, the GSK3β inhibitor consists of, or consists essentially of, at least one ingredient selected from the group consisting of 9-ING-41, HY-130795, TWS119, Tideglusib, SAR502250, AR-A014418, TDZD8, Kenpaullone, Cromoyb sodium, SB415286, IM-12, CP21R7, GNF4877, 1-Azakenpaullone, and Indirubin-3'-monoxime.

In some instances, at least a portion of the applying step is performed simultaneously with at least a portion of the administering step. In some instances, the applying step has a duration of at least 24 hours, 48 hours, 72 hours, 7 days, 14 days, 30 days or longer. The applying step can be continuous or discontinuous with breaks (e.g., breaks at 1, 2, 3, 6, 12, or 24 hours).

In some instances, the frequency of the alternating electric fields is between 50 and 1 MHz, between 75 and 500 kHz, between 80 kHz and 300 kHz, between 100 kHz and 200 kHz, or 150 kHz.

In some instances, the neurodegenerative disorder is Alzheimer's disease, Parkinson's disease, dementia, or amyotrophic lateral sclerosis (ALS).

In another aspect, a third method is provided comprising treating a neurodegenerative disorder in a subject by administering an anti-amyloid monoclonal antibody to the subject and applying alternating electric fields to the brain of the subject.

In some instances, the anti-amyloid monoclonal antibody is Aducanumab.

In some instances, at least a portion of the applying step is performed simultaneously with at least a portion of the administering step. In some instances, the applying step has a duration of at least 24 hours, 48 hours, 72 hours, 7 days, 14 days, 30 days or longer. The applying step can be continuous or discontinuous with breaks (e.g., breaks at 1, 2, 3, 6, 12, or 24 hours).

In some instances, the frequency of the alternating electric fields is between 50 and 1 MHz, between 75 and 500 kHz, between 80 kHz and 300 kHz, between 100 kHz and 200 kHz, or 150 kHz.

In some instances, the neurodegenerative disorder is dementia, ALS, Alzheimer's disease or Parkinson's disease.

In a further aspect, a fourth method is provided comprising treating a neurodegenerative disorder (e.g., Parkinson's disease) in a subject by administering one or more of levodopa (1-3,4-dihydroxyphenylalanine) and carbidopa (N-amino-α-methyl-3-hydroxy-L-tyrosine monohydrate) to the subject and applying alternating electric fields to the brain of the subject.

In some instances, at least a portion of the applying step is performed simultaneously with at least a portion of the administering step. In some instances, the applying step has a duration of at least 24 hours, 48 hours, 72 hours, 7 days, 14 days, 30 days or longer. The applying step can be continuous or discontinuous with breaks (e.g., breaks at 1, 2, 3, 6, 12, or 24 hours).

In some instances, the frequency of the alternating electric fields is between 50 and 1 MHz, between 75 and 500 kHz, between 80 kHz and 300 kHz, between 100 kHz and 200 kHz, or 150 kHz.

In a further aspect, a fifth method is provided comprising treating a neurodegenerative disorder (e.g., ALS, Parkinson's disease, Alzheimer's disease, dementia) in a subject by administering a therapeutic drug to the subject and applying alternating electric fields to the brain of the subject.

In some instances the therapeutic drug is one or more of ciprofloxacin, celecoxib, tauroursodeoxycholic acid, and sodium phenylbutyrate. For example, the therapeutic drug may include a combination of ciprofloxacin and celecoxib.

For example, the therapeutic drug may include a combination of tauroursodeoxycholic acid and sodium phenylbutyrate.

In some instances the therapeutic drug is a dopamine agonist. Suitable dopamine agonists include, but are not limited to, one or more of pramipexole, ropinirole, rotigotine, and apomorphine.

In some instances the therapeutic drug is a monoamine oxidase type B (MAO-B) inhibitor. Suitable MAO-B inhibitors include, but are not limited to, selegiline, rasagiline, and safinamide.

In some instances the therapeutic drug is a catechol O-methyltransferase inhibitor. Suitable catechol O-methyltransferase inhibitors include, but are not limited to, one of more of entacapone, opicapone, and tolcapone.

In some instances the therapeutic drug is an anticholinergic. Suitable anticholinergics include, but are not limited to, one or more of benztropine and trihexyphenidyl.

In some instances the therapeutic drug is amantadine. In other embodiments the therapeutic drug is one or more of riluzole and edaravone.

In some instances, the neurodegenerative disorder is dementia, ALS, Alzheimer's disease or Parkinson's disease.

In some instances, at least a portion of the applying step is performed simultaneously with at least a portion of the administering step. In some instances, the applying step has a duration of at least 24 hours, 48 hours, 72 hours, 7 days, 14 days, 30 days or longer. The applying step can be continuous or discontinuous with breaks (e.g., breaks at 1, 2, 3, 6, 12, or 24 hours).

In some instances, the frequency of the alternating electric fields is between 50 and 1 MHz, between 75 and 500 kHz, between 80 kHz and 300 kHz, between 100 kHz and 200 kHz, or 150 kHz.

In some instances, a therapeutic drug (e.g., GSK3β inhibitor, cholinesterase inhibitor, anti-amyloid monoclonal antibody, 1-3,4-dihydroxyphenylalanine, etc.) is provided to a subject in a therapeutically effective amount. The term "therapeutically effective amount," as used herein, refers to an amount of a drug or dose of drug sufficient to achieve its intended purpose to ameliorate, prevent, treat, or cure the disease or condition indicated. A therapeutically effective amount of a drug can be determined, for example, by one of ordinary skill in the art, from a drug or product label or from results of experiments or clinical trials designed to determine the therapeutically effective dose, pharmacokinetic, or other properties of a drug.

For example, a person of skill in the art can determine a therapeutically effective dose for a drug by consulting the drug label as approved by the U.S. Food and Drug Administration (FDA). A person of ordinary skill in the art can consult a product label approved by the FDA or other regulatory authority for any approved drug or treatment referenced herein. The term "treating," as used herein, refers to prescribing, administering, or directing others to administer a drug or treatment to a subject.

In some aspects, application of the electrical field could be interrupted by breaks. For example, 6 sessions with a duration of 12 hours each, with a 2-hour break between sessions. In another aspect, the step of applying an electrical field has a duration of at least 3 hours. In some instances, alternating electric fields can be applied for 24, 48, 72 hours or longer at 150 kHz at an intensity of 175 V/m (RMS).

In some aspects, the intensity of the alternating electric fields is 0.1 V/cm to 20 V/cm (RMS) or 1.0 V/cm to 2.5 V/cm (RMS).

In yet another aspect, the frequency of the alternating electric field is between 50 and 1 MHz, between 100 and 500 kHz, 125 to 175 kHz, or 150 kHz. In another aspect, the drug is delivered to the tissue, location, or cells at a therapeutically effective concentration, and the alternating electric field has a field strength of at least 1 V/cm in at least some of the tissue, location, or cells.

In yet another aspect, at least a portion of the applying step is performed simultaneously with at least a portion of the administering step.

Further aspects provide methods of treating a neurodegenerative disorder (e.g., Alzheimer's disease, Parkinson's disease, dementia, ALS) in a human subject comprising applying alternating electric fields to a brain of the human subject wherein the brain is tumor-free.

In some instances, the applying step has a duration of at least 24 hours, 48 hours, 72 hours, 7 days, 14 days, or 30 days. As described herein, alternating electric fields inactivate or reduce activity of GSK3β and can be used to treat a neurodegenerative disorder (e.g., Alzheimer's disease, Parkinson's disease, dementia, ALS). Neurodegenerative disorders can be slowly progressing diseases and therefore, in some instances, alternating electric fields can be applied for longer durations (e.g., at least 30 days or longer).

In some instances, a frequency of the alternating electric fields is between 50 kHz and 1 MHz, e.g., between 50 and 500 kHz.

FIG. 1 is an exemplary Western immunoblot showing the levels of GSK3β and phosphorylated GSK3β (anti pGSK3β Ser9) following treatment with alternating electric fields for a duration of 72 hours. The analysis was performed in the following cell lines: A2780 (ovarian carcinoma), A549 (lung epithelial carcinoma), Hela (cervical epithelial adenocarcinoma) and MSTO (metastatic lung cancer). As shown in FIG. 1, application of alternating electric fields (+) for 72 hours increased the level of pGSK3β Ser9 compared to control cells which did not receive application of alternating electric fields (−), which indicates inactivation or reduced activity of GSK3β.

Figure 2:
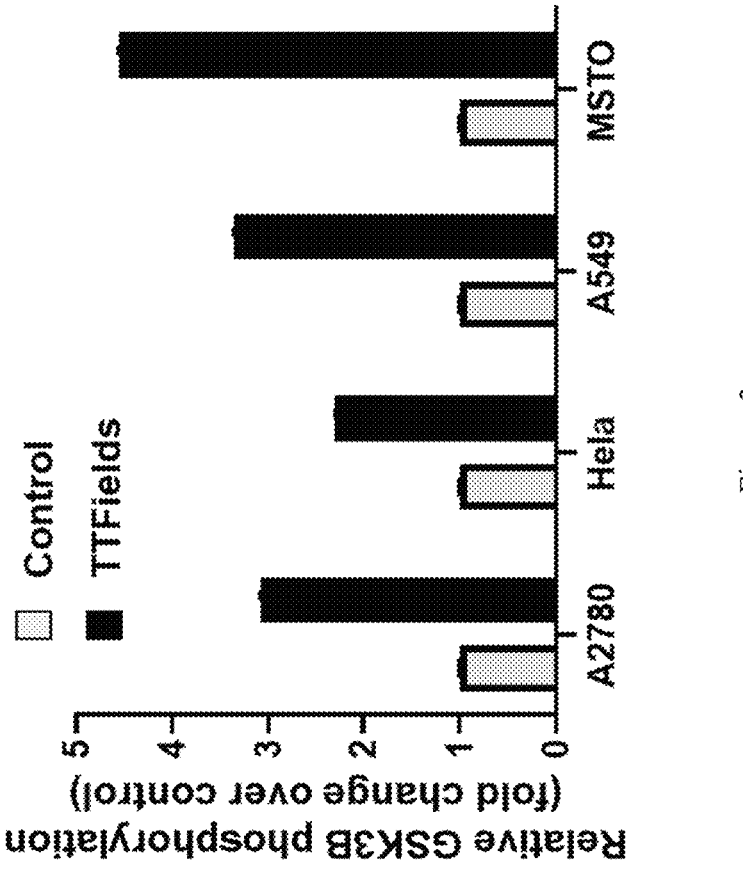
FIG. 2 provides quantification of normalized relative levels of pGSK3β (Ser9) compared to total GSK3β and GAPDH in each cell line analyzed in FIG. 1.

FIG. 2 provides a graphical representation of the quantification of western blot band intensity (FIG. 1) and their relative values to housekeeping gene (GAPDH) in control samples. Treatment with alternating electric fields increased the level of phosphorylated GSK3β relative to the GAPDH control in A2780 (ovarian carcinoma), A549 (lung epithelial carcinoma), Hela (epithelial cervix adenocarcinoma) and MSTO (lung metastatic carcinoma) cell lines, indicating that alternating electric fields inactivate or reduce the activity of GSK3β. Fiji ImageJ software was applied to measure the band intensities of Western blots. In one aspect, an increase in serine 9 phosphorylation is indicative of inhibition of GSK3β activity. As discussed above, inactivating or reducing activity of GSK3β can be used as a treatment for neurodegenerative disorders such as Alzheimer's disease, Parkinson's disease, and dementia.

Figure 3:
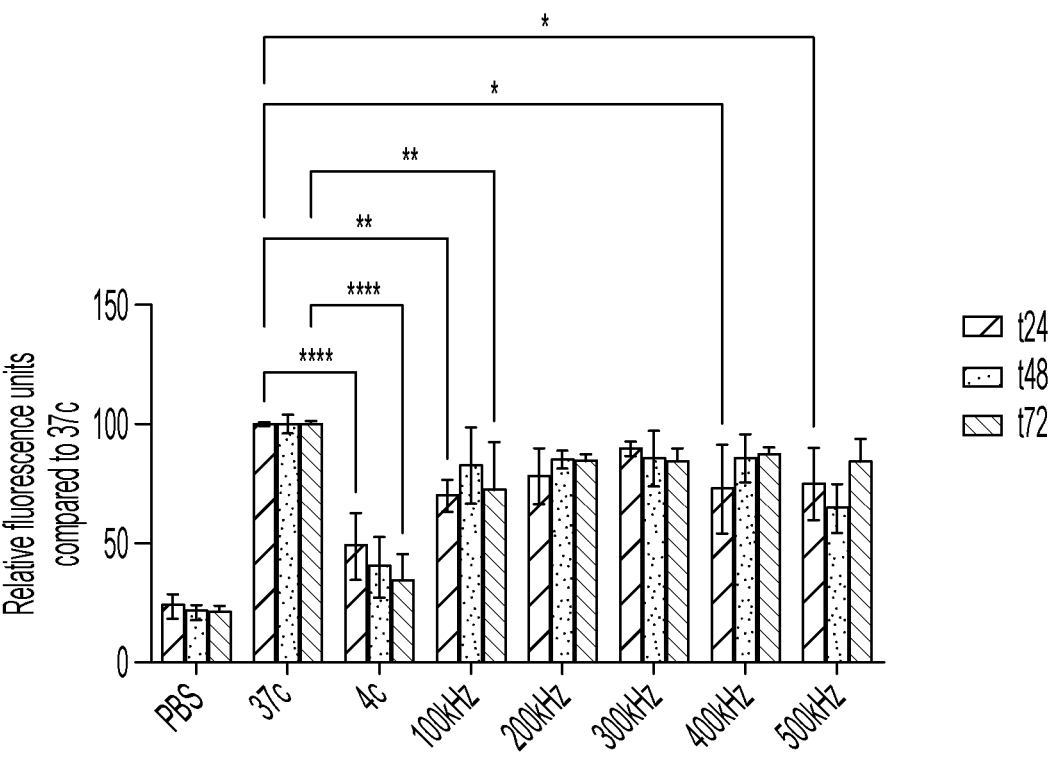
FIG. 3 depicts cell free assays of amyloid beta aggregation following treatment with TTFields at various frequencies.

FIG. 3 depicts cell free assays of amyloid beta aggregation following treatment with TTFields at various frequencies (100, 200, 300, 400, 500 kHz) for 24, 48, and 72 hours. Thioflavin T (ThT) intensities of amyloid beta samples treated with TTFields at the aforementioned frequencies were compared to ThT intensities of samples that were not exposed to TTFields and incubated at 37° C. (positive control) or 4° C. (negative control). PBS alone served as a negative control (background). As shown in FIG. 1, treatment with TTFields for 72 hours decreased the aggregation signal of amyloid beta compared to the positive control. (The results represent the average of two independent experiments. Statistical analysis *P<0.05; P<0.01, **P<0.0001; Two-way ANOVA, Sidak's test).

Amyloid beta peptides were prepared by dissolving HFIP treated human amyloid beta (Sigma-Aldrich AG968) in DMSO (180 ul) and further diluting in PBS to a final concentration of 10 uM. The samples were treated with TTFields for a total duration of 72 hours (1.62 V/cm, 37° C.) at various frequencies (100, 200, 300, 400, 500 kHz). Incubation of the amyloid beta peptides at 4° C. served as a negative control of amyloid beta fibrillation and at 37° C. as a positive control of amyloid beta fibrillation.

Thioflavin T (ThT) is a cationic benzothiazole dye that shows enhanced fluorescence upon binding to amyloid. ThT (Sigma-Aldrich T3516) was added to the samples and measured at room temperature (approx. 24° C.) using a SYNERGY/H1 plate reader (BioTek) through the top of the black 96 well plate with excitation filter of 450 nm and emission filter of 482 nm at each time point (24, 48, 72 hr).

Cell Lines and Cultures

All cell lines were obtained from ATCC (A2780 (human ovarian cancer cell line) Hela (cervical carcinoma), MSTO and A549 (human lung cancer carcinoma)). Cells were cultured in Dulbecco's modified Eagle's medium (Biological Industries) RPMI (GIBCO), F12K (ATCC) medium supplemented with 10% fetal bovine serum and antibiotics.

TTFields Application

TTFields were applied to cell cultures using the Inovitro™ system (Novocure Ltd) as previously described. Cells were seeded on cover slips at a density of 5000-20,000 cells in 500 μL and treated at predetermined exemplary optimal frequencies (e.g., A2780 (200 kHz), MSTO (150 kHz), Hela (200 kHz), and A549 (150 kHz)) at the same nominal intensity (e.g., 1.75 V/cm RMS). TTFields were applied from two directions, which were changed by 90° every 1 s as previously described. Culture media (2 ml per dish) was added 24 hours after seeding and covered in Parafilm (P7793, Sigma Aldrich) to avoid evaporation of media.

Cell Lysates and Immunoblotting

Cell extracts were prepared using RIPA lysis buffer (R0278, Sigma-Aldrich), supplemented with a cocktail of protease (Complete Mini, Roche), and phosphatase inhibitors (Halt #78420, Thermo Scientific). After determining protein concentration (BCA protein assay kit, ab102536 Abcam), 30 μg protein was resolved by SDS-polyacrylamide gel electrophoresis (Bolt 12% Bis-Tris base gel NW00080BOX, Thermo-Fischer) under reducing conditions (Bolt Sample reducing agent, #2060435 and Sample buffer #2045289, Novex). After electrophoresis, proteins were transferred to polyvinylidene difluoride membrane (Bio-Rad) and probed with the appropriate primary antibody (GAPDH (SC-32233, Santa Cruz), GSK3β (cell signalling, 9832S) and pGSK3β Ser9 (cell signalling, 5558S)) followed by horseradish peroxidase-conjugated secondary antibody (goat anti rabbit 7074, Cell Signalling and goat anti mouse 7076, Cell Signalling) and a chemiluminescent substrate (WBLUF0100, Signa-Aldrich). Quantification of bands was done by Image J software.

The in vitro experiments described herein were carried out using the Novocure Inovitro™ system. In these experiments, the direction of the alternating electric fields was switched at one second intervals between two perpendicular directions. But in alternative embodiments, the direction of the alternating electric fields can be switched at a faster rate (e.g., at intervals between 1 and 1000 ms) or at a slower rate (e.g., at intervals between 1 and 100 seconds).

In the in vitro experiments described herein, the direction of the alternating electric fields was switched between two perpendicular directions by applying an AC voltage to two pairs of electrodes that are disposed 90° apart from each other in 2D space in an alternating sequence. But in alternative embodiments, the direction of the alternating electric fields may be switched between two directions that are not perpendicular by repositioning the pairs of electrodes, or between three or more directions (assuming that additional pairs of electrodes are provided). For example, the direction of the alternating electric fields may be switched between three directions, each of which is determined by the placement of its own pair of electrodes. Optionally, these three pairs of electrodes may be positioned so that the resulting fields are disposed 90° apart from each other in 3D space. In other alternative embodiments, the electrodes need not be arranged in pairs. See, for example, the electrode positioning described in U.S. Pat. No. 7,565,205, which is incorporated herein by reference. In other alternative embodiments, the direction of the field remains constant.

In the in vitro experiments using the Inovitro™ system described herein, the electrical field was capacitively coupled into the culture because the Inovitro™ system uses conductive electrodes disposed on the outer surface of the dish sidewalls, and the ceramic material of the sidewalls acts as a dielectric. But in alternative embodiments, the electric field could be applied directly to the cells without capacitive coupling (e.g., by modifying the Inovitro™ system configuration so that the conductive electrodes are disposed on the sidewall's inner surface instead of on the sidewall's outer surface).

The methods described herein can also be applied in the in vivo context by applying the alternating electric fields to a target region of a live subject's body (e.g., using the Novocure Optune® system). This may be accomplished, for example, by positioning electrodes on or below the subject's skin so that application of an AC voltage between selected subsets of those electrodes will impose the alternating electric fields in the target region of the subject's body.

For example, in situations where the relevant cells are located in the subject's brain, one pair of electrodes could be positioned on the front and back of the subject's head, and a second pair of electrodes could be positioned on the right and left sides of the subject's head. In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body. In another embodiment, electrodes could be inserted subcutaneously below a patient's skin. An AC voltage generator applies an AC voltage at a selected frequency (e.g., 200 kHz) between the right and left electrodes for a first period of time (e.g., 1 second), which induces alternating electric fields where the most significant components of the field lines are parallel to the transverse axis of the subject's body.

Then, the AC voltage generator applies an AC voltage at the same frequency (or a different frequency) between the front and back electrodes for a second period of time (e.g., 1 second), which induces alternating electric fields where the most significant components of the field lines are parallel to the sagittal axis of the subject's body. This two-step sequence is then repeated for the duration of the treatment. Optionally, thermal sensors may be included at the electrodes, and the AC voltage generator can be configured to decrease the amplitude of the AC voltages that are applied to the electrodes if the sensed temperature at the electrodes gets too high. In some embodiments, one or more additional pairs of electrodes may be added and included in the sequence. In alternative embodiments, only a single pair of electrodes is used, in which case the direction of the field lines is not switched. Note that any of the parameters for this in vivo embodiment (e.g., frequency, field strength, duration, direction-switching rate, and the placement of the electrodes) may be varied as described above in connection with the in vitro embodiments. But care must be taken in the in vivo context to ensure that the electric field remains safe for the subject at all times.

Note that in the experiments described herein, the alternating electric fields were applied for an uninterrupted interval of time (e.g., 72 hours). But in alternative embodiments, the application of alternating electric fields may be interrupted by breaks that are preferably short. For example, a 24-hour interval of time could be satisfied by applying the alternating electric fields for six 4 hour blocks, with 1 or 2 hour breaks between each of those blocks.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the claims listed below, and equivalents thereof.

What is claimed is:

1. A method of treating a neurodegenerative disorder in a subject consisting essentially of applying alternating electric fields to a brain of the subject to reduce activity of GSK3β, wherein the alternating electric fields have an intensity of 1 V/cm to 20 V/cm (RMS) and a frequency between 50 kHz and 1 MHz, and wherein the neurodegenerative disorder is Alzheimer's disease (AD), amyotrophic lateral sclerosis (ALS), dementia, or Parkinson's disease.

2. The method of claim 1, wherein the applying step has a duration of at least 24 hours.

3. The method of claim 1, wherein the applying step has a duration of at least 72 hours.

4. The method of claim 1, wherein the applying step has a duration of at least 30 days.

5. The method of claim 1, wherein the intensity is 1.0 V/cm to 2.5 V/cm (RMS).

6. The method of claim 1, wherein the brain is tumor-free.

7. The method of claim 1, further comprising diagnosing the subject with a neurodegenerative disorder.

8. The method of claim 1, wherein the subject is not diagnosed as having a tumor prior to applying the alternating electric fields.

* * * * *